United States Patent [19]

Neidigh

[11] 4,109,507

[45] Aug. 29, 1978

[54] RECIRCULATING SHOT TESTING DEVICE
[75] Inventor: Robert J. Neidigh, Bremen, Ind.
[73] Assignee: Wheelabrator-Frye Inc., Mishawaka, Ind.
[21] Appl. No.: 825,092
[22] Filed: Aug. 16, 1977
[51] Int. Cl.² ............................................... G01N 3/08
[52] U.S. Cl. .......................................... 73/12; 51/424; 51/432; 73/7
[58] Field of Search ................... 73/7, 12, 86; 51/424, 51/432

[56] References Cited

U.S. PATENT DOCUMENTS

| | | | |
|---|---|---|---|
| 1,480,575 | 1/1924 | Snider | 51/424 X |
| 2,422,179 | 6/1947 | Brewster | 73/7 X |
| 3,229,498 | 1/1966 | Oakes | 73/7 |
| 3,900,969 | 8/1975 | Diehn | 51/432 X |

Primary Examiner—Charles Gorenstein
Attorney, Agent, or Firm—McDougall, Hersh & Scott

[57] ABSTRACT

A device is disclosed for testing the useful life of particulates, such as, steel shot, grit or other abrasives. The device employs a blast wheel for throwing the shot at high velocity against an annular target. The wheel and target are mounted on a rotating structure so that substantially all of the spent particulate is continually returned to the wheel via a recirculating tube. In this manner accurate evaluation of a particulate sample under test can be accomplished.

8 Claims, 4 Drawing Figures

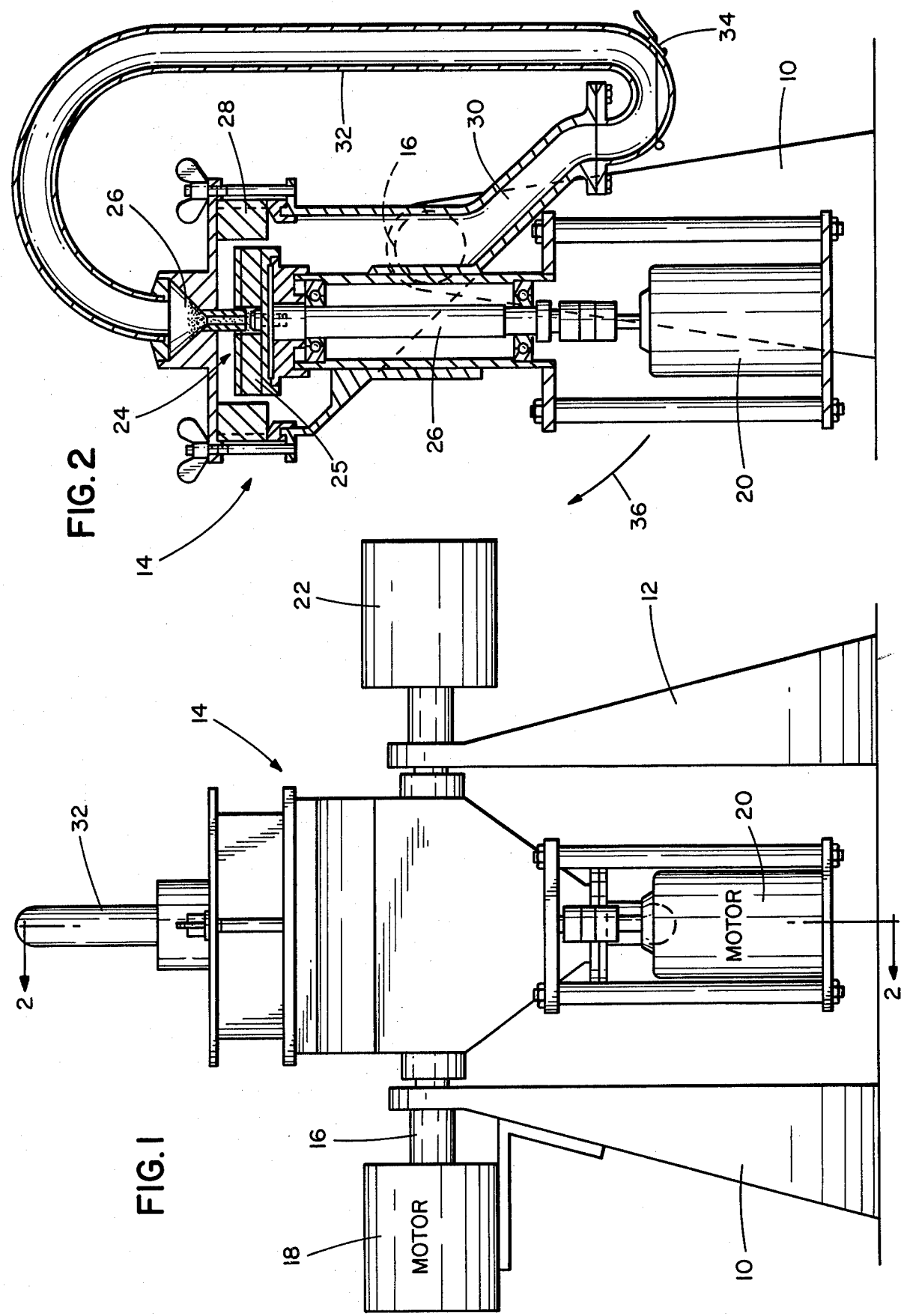

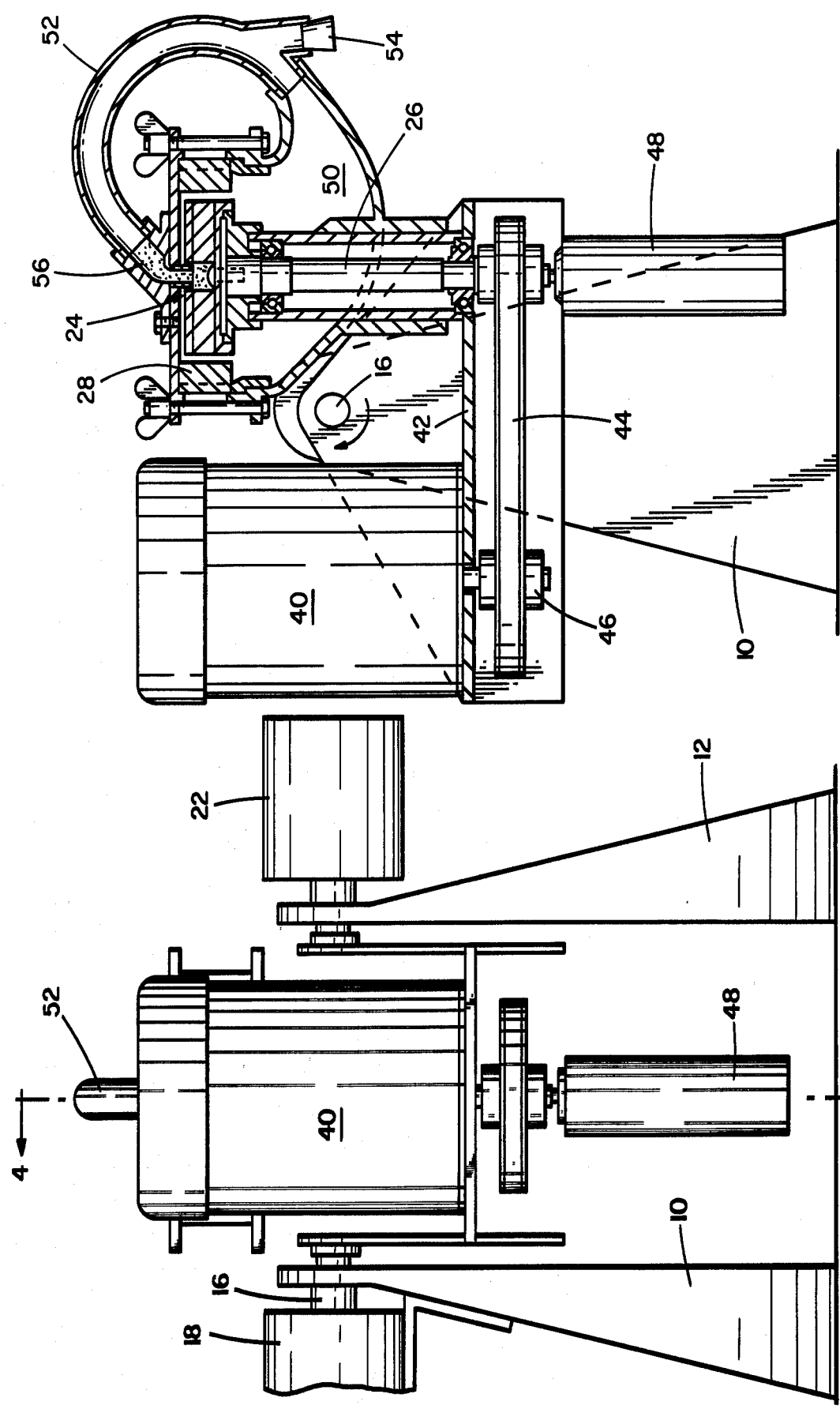

RECIRCULATING SHOT TESTING DEVICE

BACKGROUND OF THE INVENTION

This invention relates to the field of particulate blasting devices. More specifically, it relates to the field of devices for throwing abrasive particulate, such as, steel shot, grit, sand and the like, against a surface to be cleaned, abraded or otherwise treated. Typical of such devices are the centrifugal blasting wheels manufactured by Wheelabrator-Frye, Inc., Mishawaka, Indiana. These devices employ particulate to accomplish the treatment operations referred to and, in most cases, recirculate substantial portions of the particulate for further treatment whereby an efficient and low cost surface treatment is accomplished. Since the abrasive must be utilized for repeated cleaning operations it is necessary to know its useful life. As abrasive is used it begins to break down into small dust-like particles and loses its effectiveness. When this happens it is necessary to replace the particulate in order to maintain the efficiency of the treatment operation.

Accordingly, it is desirable to evaluate various kinds of particulate and even specific samples of a particular type to insure uniformity and that the particulate is up to specification. The present invention relates to a testing device capable of evaluating the useful life of a given sample of particulate. Shot testers, as they are often referred to, are known. However, the prior devices did not include structure for effecting substantially complete recirculation of the entire sample to insure reliability of the test results. Such prior devices are not necessarily closed systems nor is there any assurance that substantially all of the shot sample will pass through the throwing wheel during each test cycle. Other disadvantages of the prior devices include lack of portability and the complexity of the mechanism.

It is accordingly an object of the present invention to provide a shot testing device which employs a closed system for recirculating the shot sample under test.

Another object of the invention is to provide a shot tester wherein substantially all of the shot sample passes through the abrasive throwing wheel during each cycle of operation.

A further object of the invention is to provide a simple but effective means for returning the spent particulate back to the throwing wheel for further testing.

Another object of the invention is to provide a simple device for testing the useful life of blasting particulate.

Other objects and advantages of the invention will be apparent from the remaining portion of the specification.

SUMMARY OF THE INVENTION

A particulate throwing wheel is mounted within a housing so that it directs a stream of particulate against an annular target. The target is shaped so as to deflect shot away from the wheel. The spent particulate is conveyed back to the wheel for further blasting by rotation of the entire blast assembly thereby assuring that all of the shot is subjected to the same number of cycles through the device.

BRIEF DESCRIPTION OF THE DRAWINGS

FIG. 1 is a front elevation of the invention according to a first embodiment.

FIG. 2 is a side elevation having portions cut away long the lines 2—2 of FIG. 1.

FIG. 3 is a front elevation of the invention according to a second and preferred embodiment.

FIG. 4 is a side elevation having portions cut away long the lines 4—4 of FIG. 3.

DETAILED DESCRIPTION

Referring to FIGS. 1 and 2, the first embodiment is illustrated. The shot tester according to the invention is mounted for rotation on a pair of arms 10 and 12 secured to the base. The tester, indicated generally by 14, is rotated on shaft 16 by a motor 18 indicated by the box in FIG. 1. A second motor 20 is provided for rotating the blast wheel. The electrical connections for motor 20 are provided by the slip ring pick up 22 in a manner well known in the art.

Referring specifically to FIG. 2, the details of the shot life tester 14 are illustrated. Motor 20 drives a particulate blast wheel 24 via drive shaft 26. The wheel 24 includes a plurality of radially extending blades 25. The particulate under test is supplied at the center point of the blades from a hopper 26. From that point it passes outwardly due to the rotation of the blades 25, gaining in velocity until it strikes the annular target 28. The particulate then drops downwardly by virtue of gravity and the geometry of the target into the trough-like enclosure 30. It will be observed that the bottom of the trough is connected by means of a flexible recirculating tube 32 back to the hopper 26. For insertion or removal of a shot sample a loading door 34 is provided. Except for the loading door the entire system is closed so that shot cannot be lost from the system in any significant amount.

As stated earlier, the entire testing device 14 is mounted for rotation and rotates in the direction indicated by arrow 36 during operation of the blast wheel 24. The speed of rotation of the device is variable by adjusting the speed of the motor 18. For most purposes a velocity of approximately 29 RPM has been found satisfactory. At this angular velocity all the spent particulate which accummulates in the trough 30 is conveyed by force of gravity and by the centrifugal force of rotation out of the trough 30 and through the recirculating tube 32 back to the hopper 26. The precise speed of rotation, of course, will depend upon several variables, such as, the size of the chamber, the type and amount of particulate under test and other factors. The proper angular velocity for a given sample is easily determined by empirical methods. At the correct angular velocity substantially all of the particulate will repeatedly pass through the blasting wheel and strike the target, be collected in trough 30 and then pass through the recirculation tube back to the hopper 26 to begin another test cycle. In this manner the useful life of a particular type of abrasive can be accurately determined by its resistance to break down as a function of time or cycles through the blast wheel.

Referring now to FIGS. 3 and 4, a second embodiment of the invention is illustrated. This embodiment closely corresponds in operation to the first embodiment, the principal difference being that this embodiment is somewhat more compact in design and is counterbalanced. Elements which are identical to the first embodiment have, for convenience, been given the same numbers in this embodiment. With particular reference to FIG. 4, it will be observed that in this embodiment the drive motor 40 is mounted to a frame 42 on the opposite side of the rotating shaft 16 from the shot life tester. Thus, the motor is used to counterbalance the shot life tester. The wheel 24 is driven by motor 40 via a belt drive 44 connecting the power take-off 46 with the shaft 26. The belt drive can also be utilized to operate a speed counter device 48 which is optional and forms no part of the present invention. The optional speed counter permits accurate setting of the wheel velocity.

In the second embodiment the trough portion of the device is somewhat bulb shaped and indicated by numeral 50 while the recirculating tube 52 is substantially shorter by virtue of the change in configuration of the device. A loading door 54 is provided for entry and exit of the sample under test. The hopper 56 for the present embodiment is offset somewhat to mate with the upper end of the recirculating tube. In all operational respects this embodiment is substantially identical to the first embodiment. That is, a shot sample is placed into the device through the door 54. The wheel is then turned on and set to an appropriate velocity. The test commences by operating motor 18 to begin rotation of the entire structure whereby substantially all of the shot under test is continually fed through the blast wheel to determine its useful life.

While I have shown and described embodiments of this invention in some detail, it will be understood that this description and illustrations are offered merely by way of example, and that the invention is to be limited in scope only by the appended claims.

I claim:

1. A device for life testing particulate comprising:
   (a) a target,
   (b) means for projecting said particulate against said target at high velocity, said target and said projecting means mounted on a frame,
   (c) means for collecting spent particulate, and
   (d) means for returning said particulate from said collecting means to said projecting means by force of gravity, said returning means including
      (i) means for rotating said frame at a selected speed,
      (ii) a recirculating tube communicating said collecting means with said projecting means,
      whereby rotation of said frame causes substantially all of said particulate to move by force of gravity from said collecting means into and through said recirculating tube back to said projecting means.

2. The device according to claim 1 wherein said target is annular.

3. The device according to claim 1 wherein said means for projecting includes a motor driven centrifugal blasting wheel and a hopper for conducting particulate from said returning means to said wheel.

4. The device according to claim 1 wherein said collecting means includes a trough disposed beneath said projecting means.

5. The device according to claim 1 wherein said rotating means includes:
   a shaft to which said frame is secured,
   a pair of arms supporting said shaft for rotation, and
   a motor for rotating said shaft.

6. The device according to claim 1 wherein said recirculating tube includes a sample door for permitting entry and removal of the particulate from the device.

7. The device according to claim 1 wherein said projecting means includes:
   a blasting wheel, and
   a motor secured to said frame for rotating said wheel at a predetermined speed.

8. The device according to claim 7 wherein said motor is positioned on said frame to counterbalance said wheel during rotation of said frame.

* * * * *